United States Patent [19]

Nambu et al.

[11] Patent Number: 4,530,220
[45] Date of Patent: Jul. 23, 1985

[54] DEFORMABLE BAG FOR USE AS COOLING MEDIUM

[75] Inventors: Masao Nambu, Yokohama; Tatsuo Kinoshita, Chigasaki, both of Japan

[73] Assignee: Nippon Oil Co., Ltd., Tokyo, Japan

[21] Appl. No.: 594,376

[22] Filed: Mar. 28, 1984

[30] Foreign Application Priority Data

Apr. 4, 1983 [JP] Japan .............................. 58-48981[U]

[51] Int. Cl.³ ................................................ F25D 3/08
[52] U.S. Cl. .......................................... 62/530; 62/457
[58] Field of Search .......................... 62/529, 530, 457; 206/219

[56] References Cited

U.S. PATENT DOCUMENTS 2,697,424 12/1954 Hanna ................................ 62/530 X
3,258,065 6/1966 Ward ................................. 62/530 X
4,404,820 9/1983 Romaine ............................. 62/530

FOREIGN PATENT DOCUMENTS 8096970 6/1983 Japan ................................... 62/529

Primary Examiner—Lloyd L. King
Attorney, Agent, or Firm—Keil & Weinkauf

[57] ABSTRACT

According to the invention, a deformable bag for use as a cooling medium is provided. The bag comprises small pieces of gel packed in a flexible envelope. The gel is prepared by casting into a mold an aqueous solution or suspension containing a polyvinyl alcohol and a water-soluble organic compound, and cooling the cast aqueous solution or suspension to −10° C. or lower and then partially, dehydrating, without thawing, the thus obtained cooled mass in vacuum. The bag of the invention can be applied on different objects or portions having various configurations.

17 Claims, 1 Drawing Figure

DEFORMABLE BAG FOR USE AS COOLING MEDIUM

BACKGROUND OF THE INVENTION

1. Field of the Invention

The present invention relates to a deformable bag for use as a cooling medium, and more particularly it relates to a cooling bag which can be deformed to fit to the contour of any portion of human or animal body so as to cover intimately the portion to be cooled thereby.

2. Prior Art

A variety of gel compositions have hitherto been proposed to be used as cooling media and some of them are applied for practical uses. Such a gel is referred to as a cooling gel, chilling gel, coldness-keeping means, coolant composition or ice pillow without the need of ice. However, these known coolant gels are extremely inconvenient in that they cannot be deformed into any desired form other than the designed forms, thus making it difficult to apply them as universal cooling media for cooling general objects, such as different portions of human body having various configurations, although they can be effectively used for cooling the target area of human body or other objects having the configuration, in conformity of which the known gels are preformed.

OBJECTS AND SUMMARY OF THE INVENTION

A primary object of this invention is to provide a deformable bag for use as a cooling medium which can be applied universally on different objects or portions having various configurations.

Another object of this invention is to provide a deformable bag for use as a cooling medium and having comfortable touch to human body.

A further object of this invention is to provide a deformable bag for use as a cooling medium, the bag comprising a plurality of small pieces of a gel having a high water content and no tendency of sticking with one another, thus being moved smoothly in the bag when the bag is deformed.

The deformable bag for use as a cooling medium, according to the present invention, comprises a plurality of small pieces of a gel having a high water content and packed in a flexible envelope, said gel being prepared by the steps of preparing an aqueous solution or suspension of a mixture of a water-soluble organic compound and a polyvinyl alcohol having a degree of hydrolysis of not less than 95 mol % and an average polymerization degree of not less than 1,100, the concentration of said organic compound in said mixture being adjusted to be in the range of from 5 to 40 wt % and the concentration of said polyvinyl alcohol in said mixture being more than 8 wt % and not more than 25 wt %, casting said aqueous solution or suspension into a mold having desired shape and dimensions, cooling the cast aqueous solution or suspension to a temperature of not higher than—(minus) 10° C. to solidify the same to form a molded mass of solidified gel, and then partially dehydrating, without thawing, the molded mass of solidified gel in vacuum until the percentage dehydration rate (the weight reduction rate of the solidified gel) reaches not less than 3 wt %.

BRIEF DESCRIPTION OF THE DRAWING

The single FIG. 1 in the appended drawing is a schematic illustration showing one embodiment of the deformable bag according to this invention.

DESCRIPTION OF THE INVENTION

Figure 1:
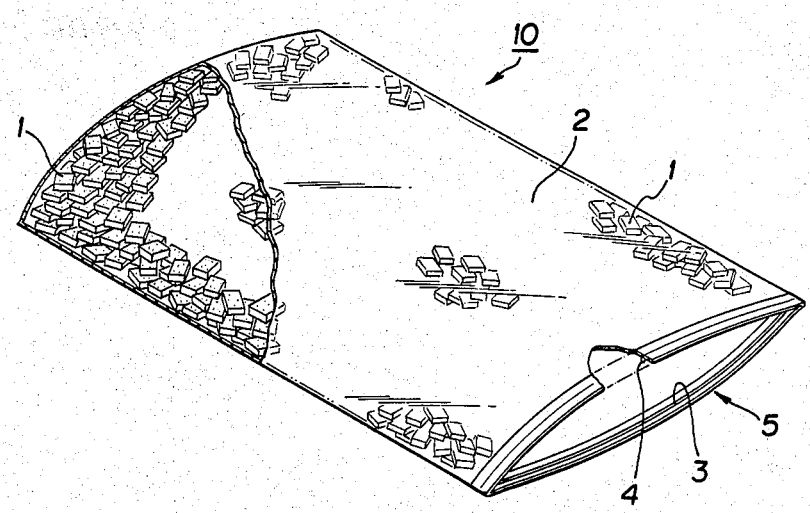

The present invention will now be described in detail hereinafter.

The polyvinyl alcohol used in the present invention should have a degree of hydrolysis of not less than 95 mol %, preferably not less than 97 mol %. If a polyvinyl alcohol having a degree of hydrolysis of 80 to 88 mol %, particularly less than 85 mol %, is used, the resultant gel is weak and crumble. A gel having rubber-like elasticity cannot be formed from a polyvinyl alcohol having such a low degree of hydrolysis. It is also essential that the polymerization degree of the used polyvinyl alcohol be not less than 1,100. If the polymerization degree of the used polyvinyl alcohol is less than the defined range, the mechanical strength of the resultant gel is lowered. It is preferred that a polyvinyl alcohol having a polymerization degree of from 1,100 to about 3,300 is used. Commercially available polyvinyl alcohol product having a polymerization degree ranging within 1,100 to 2,600 may be used.

In the first step for the preparation of the bag according to the invention, an aqueous solution or suspension containing the aforementioned polyvinyl alcohol and a water-soluble organic compound is prepared. The concentration of polyvinyl alcohol in the aqueous solution or suspension should be more than 8 wt % and not more than 25 wt %, preferably in the range of from 9 to 15 wt %. If the concentration of polyvinyl alcohol is more than 25 wt %, the resultant gel becomes too hard and gives somewhat uncomfortable touch when used as a cooling medium. On the contrary, if the concentration of polyvinyl alcohol is less than 8 wt %, the resultant gel is too weak to crumble away during the use as a cooling medium.

According to one important aspect of the present invention, a water soluble organic compound is added to the aqueous solution of aforementioned polyvinyl alcohol prior to gelation. The water-soluble organic compound added to the solution of polyvinyl alcohol is selected from those which are used as antifreezing agents, and acts as the freezing point depressing agent. Examples of water-soluble organic compounds, which may be used in preparation of the gel contained in the bag of the invention, are water-soluble monohydric alcohol and derivatives thereof, such as methyl alcohol, ethyl alcohol and isopropyl alcohol; water-soluble polyhydric alcohols, such as ethylene glycol, propylene glycol, 1,3-propylene glycol, glycerin, and 2-methyl 2,4-pentanediol; and other water-soluble organic compounds, such as acetone, dimethylsulfoxide, methylsulfonic acid, ethylsulfonic acid, dimethylamine, methylamine and formic acid. Further examples of suitable compounds are monosaccharides, such as erythritol, arabinose, xylose, xylitol, glucose, glucitol (sorbitol or sorbite), gluconic acid, glucuronic acid, glucaric acid, galacturonic acid, fructose and glucosamine; disaccharides, such as sucrose, cellobiose and lactose; trisaccharides, such as raffinose; and water-soluble polysaccharides, such as agarose, amylose, sodium alginate, glycogen, chondroitin, chondroitin sulfuric acid, dextran, pectic acid, propylene glycol alginate, tragacanth gum, pullulan, and chondroitin sodium sulfate. Ethylene glycol, propylene glycol, glycerin and D-sorbitol are particularly preferred, since they are odorless and less volatile and have the advantage that the freezing point of the admixture can be depressed by adding a relatively small quantity thereof with appreciable contribution to improvement in mechanical strength of the resultant gel.

The concentration of the aforementioned water-soluble organic compound in the aqueous solution or suspension should be within the range of from 5 to 40 wt %, preferably from 10 to 35 wt %. If the concentration thereof is lower than 5 wt %, it becomes difficult to lower the freezing point of the solution below $-10°$ C. If the concentration thereof is higher than 40 wt %, the freezing point of the solution is excessively lowered or the freezing point is rather raised. Anyway, excess addition of the water-soluble organic compound increases economical expense with no technical merit. By the addition of the afore-mentioned water-soluble organic compound, the freezing point of the gel is depressed below $-20°$ C., and thus the gel may be cooled in an ice-box (generally maintained at a temperature of from $-10°$ to $-20°$ C.) of a general household refrigerator without being frozen to retain the elasticity and soft touch resembling the living tissues.

In preparation of the aforementioned aqueous solution or suspension containing both of the polyvinyl alcohol and the water-soluble organic compound acting as the antifreezing agent; the polyvinyl alcohol and one or more of the water-soluble organic compounds are added to water simultaneously to be dissolved or suspended in water; the polyvinyl alcohol is initially dissolved in water and then the solution is added to the water-soluble organic compound or an aqueous solution thereof; or the water-soluble organic compound or an aqueous solution thereof is mixed with an aqueous solution of the polyvinyl alcohol or mixed with the polyvinyl alcohol of powder form. Irrespective of the method adopted for the preparation of the solution or suspension, the concentration of polyvinyl alcohol is adjusted to be within the range of more than 8 wt % and not more than 25 wt % and the concentration of water-soluble organic compound is adjusted to be within the range of from 5 to 40 wt %.

In the present invention, the aqueous solution or suspension containing the aforementioned polyvinyl alcohol and the aforementioned water-soluble organic compound is cast into a mold having desired shape and dimensions followed by cooling to obtain a molded mass of solidified gel.

At the cooling step, the aqueous solution or suspension is cooled to a temperature of lower than $-10°$ C., using a coolant selected from cryogens, such as sodium chloride-ice (23:77, $-21°$ C.) and calcium chloride-ice (30:70, $-55°$ C.), dry ice-methyl alcohol ($-72°$ C.) and liquefied nitrogen ($-196°$ C.). Although the aqueous solution or suspension may be cooled to $-269°$ C. by the use of liquefied helium, the use of liquefied helium is not recommendable from the economical viewpoint without any merit for improving the quality of the resultant gel. In practical operation, a freon refrigerator is used to cool the solution or suspension to a temperature of from $-20°$ C., to $-80°$ C. The cast solution or suspension may be, of course, cooled in an ice-box (maintained at $-10°$ C. to $-20°$ C.) of a household refrigerator. The cooled mass is then subjected to dehydration in vacuum to form a solidified gel. The cast mass should be cooled sufficiently, since insufficient cooling results in inferior mechanical strength of the resultant gel.

Accordingly, in the present invention, the aqueous solution or suspension containing the polyvinyl alcohol and one or more water-soluble organic compounds should be cooled to below $-10°$ C., preferably below $-15°$ C.

According to another important aspect of the invention, the cooled mass is then dehydrated in vacuum without thawing. The mechanical strength of the gel is improved as the percentage dehydration rate (i.e. the weight reduction rate of the cooled and solidified gel) is increased. However, in view of the application as the cooling medium, it is not necessary to increase the percentage dehydration rate so high as to obtain a gel having extremely high mechanical strength. It is preferred, in consideration of the softness and elasticity of the resultant gel, that the percentage dehydration rate be controlled not less than 3 wt %, preferably within the range of from 3 wt % to 35 wt %. The dehydration in vacuum means the dehydration under a reduced pressure. The pressure is not particularly a critical parameter, and dehydration may be effected at a pressure of not higher than 1 mmHg, preferably not higher than 0.1 mmHg and more preferably not higher than 0.08 mmHg.

In the present invention, small pieces of solidified gel are formed from the thus obtained gel having a high water content by casting the aqueous solution or suspension containing the polyvinyl alcohol and one or more water-soluble organic compounds into a plurality of molds for molding small pieces of molded mass having desired shape and dimensions. Otherwise, a molded mass having larger dimensions may be cut to a plurality of small pieces having desired shape and dimensions. The shape of small pieces of high water content gel is not limited and may be cubic, rectangular parallelepiped cylindrical or spherical. The dimensions of the gel pieces are not critical, and it suffices that each piece is small enough to move smoothly in the envelope to deform the bag. It is generally preferable that each piece has the dimensions, i.e. the length of each side or diameter, ranging within 2 mm to 5 cm.

A plurality of small pieces of the gel having high water content is put into a flexible envelope and the opening of the envelope is closed. Preferable materials for the flexible envelope include plastic films, such as polyethylene, polypropylene and polyvinylchloride films. These films are preferred because they provide comfortable touch to human body and durable sealing properties.

Small pieces of high water content gel are packed in the envelope such that about 50 to 90 vol % of the space enclosed by the envelope is occupied by the packed gel pieces. The volume percentage occupied by the packed gel pieces is not a critical parameter, provided that the packed gel pieces are movable within the envelope to realize deformation of the bag. The shape and dimensions of the bag are not limited. For example, a rectangular parallelepiped bag having the dimensions of $20 \times 15 \times 4$ cm may be prepared and used generally for cooling any desired portion of human body. The doubled or tripled envelopes may be used to prevent the enclosed gel pieces from getting out of the envelope even when one of the envelope is broken.

To close the opening of the envelope, fastener means including a groove extending along one side edge of the opening and a projection extending along the opposing side edge of the opening may be provided to engage with each other after the gel pieces are packed in the envelope. When an envelope made of a plastic film is used, the opening of the envelope may be closed by hot melting. Otherwise, the opening of the envelope may be tied up by means of a string or cord, or the end of the opening may be folded and then sewn together. The opposing faces of the edge of the envelope may be joined together using an adhesive. The gel pieces of high water content are enclosed in the envelope by any means.

The envelope may be provided with a cord or strip for tying each other after the bag is applied to a desired portion to be cooled. The cord or strip may be provided with a "velcro" fastener (Trade Mark), which is a material having a surface with projecting fibers for releasably engaging projecting fibers on another surface. Alternatively, the bag may be fixed by winding a bandage around the bag.

The bag according to this invention comprises a plurality of small gel pieces movably enclosed in an envelope, and can be deformed freely after it is cooled so that it covers intimately any curved portion, such as throat, leg, arm, head, auricular region, inguen chin, eyelid, face, axillary region or breast, to cool effectively the portion on which it is placed.

EXAMPLE OF THE INVENTION

A preferred embodiment of this invention will now be described with reference to the appended drawing.

EXAMPLE 1 kg of a 10 wt % aqueous solution of a polyvinyl alcohol having a degree of hydrolysis of 99.5 mol %, an average polymerization degree of 2,600 and a viscosity at 20° C. of a 4% aqueous solution of 67 centipoises was mixed with 500 g of propylene glycol. The mixture was cast into a stainless steel mold, and cooled at −42° C. for 14 hours. The cooled mass was then subjected to dehydration in vacuum without thawing to remove 200 g of water, followed by allowing to stand at room temperature, to obtain a rectangular parallelepiped gel having the dimensions of 24 cm×20 cm×2.7 cm.

The gel mass was cut into parallelepiped pieces having average dimensions of 1 cm×1.2 cm×0.3 cm. About 3500 small pieces 1 were prepared. The small pieces 1 (about 3000 pieces) of the gel were packed in a polyethylene envelope 2 (20 cm×15 cm×4 cm) so that about 75 vol % of the space enclosed by the envelope 2 was occupied by the packed gel pieces. The envelope 2 was provided with a groove 3 and a projection 4 extending along the edges of the opening of the envelope 2 to form fastener means 5. After packing the gel pieces 1, the fastener means 5 was closed to sealingly enclose the gel pieces to prepare a bag 10 adapted for use as a cooling medium.

The thus prepared cooling bag 10, according to the present invention, was allowed to stand in an icebox (maintained at −22° C.) of a refrigerator for 2 days to reveal that the small gel pieces 1 did not become rigid and retained the softness and elasticity.

The cooled bag 10 was placed on the throat of a patient to reveal that the bag 10 was deformed in conformity with the contour of the throat portion to cover intimately and to cool effectively the applied portion. The final composition of the gel was composed of 7.5 wt % of polyvinyl alcohol, 38 wt % of propylene glycol and 54 wt % of water.

In the foregoing description, the present invention has been specifically disclosed by referring to an example thereof. However, it should be appreciated that various modifications and variations can be easily made by those skilled in the art without departing from the spirit of the invention. It is, thus, intended to include all such modifications and variations within the wide scope of the present invention defined by the appended claims.

What is claimed is:

1. A deformable bag for use as a cooling medium which comprises:
  (a) A flexible envelope, and
  (b) A plurality of small pieces of a polyvinyl alcohol gel having a high water content packed within said envelope, said gel having been prepared by the steps of forming an aqueous solution or suspension of a mixture of a water-soluble organic compound and a polyvinyl alcohol having a degree of hydrolysis of not less than 95 mol % and an average polymerization degree of not less than 1,100, the concentration of said organic compound in said mixture being adjusted to be in the range of from 5 to 40 wt % and the concentration of said polyvinyl alcohol in said mixture being more than 8 wt % and not more than 25 wt %, casting said aqueous solution or suspension into a mold having the desired shape and dimensions, cooling the cast aqueous solution or suspension to a temperature of no higher than −(minus) 10° C. to solidify the same to form a molded mass of solidified gel, and then partially dehydrating, without thawing, the molded mass of solidified gel in vacuum until the percentage dehydration rate (the weight reduction rate of the solidified gel) reaches not less than 3 wt %.

2. The deformable bag of claim 1, wherein said water soluble organic compound is selected from the group consisting of water-soluble monohydric alcohols and derivatives thereof, water-soluble polyhydric alcohols, monosaccharides, disaccharides, trisaccharides, water soluble polysaccharides, and mixtures thereof.

3. The deformable bag of claim 2, wherein said water soluble organic compound is selected from the group consisting of ethylene glycol, propylene glycol, glycerin, D-sorbitol, and mixtures thereof.

4. The deformable bag of claim 1, wherein said water soluble organic compound is selected from the group consisting of acetone, dimethyl-sulfoxide, methylsulfonic acid, ethylsulfonic acid, dimethylamine, methyl amine, formic acid, and mixtures thereof.

5. The deformable bag of claim 1, wherein said step of partial dehydration is effected at a reduced pressure of not higher than 1 mmHg.

6. The deformable bag of claim 1, wherein said mold having desired shape and dimensions includes a plurality of mold sections for molding small pieces of gel of finished shape and dimensions.

7. The deformable bag of claim 1, wherein said mold having desired shape and dimensions is a mold for molding a gel mass of larger dimensions, and said gel mass of larger dimensions is cut to form a plurality of said small pieces of said gel.

8. The deformable bag of claim 1, wherein each of said small pieces of said gel has the dimensions ranging within 2 mm to 5 cm.

9. The deformable bag of claim 1, wherein said envelope is made of a plastic film.

10. The deformable bag of claim 9, wherein the opening of said envelope are closed by hot melting.

11. The deformable bag of claim 1, wherein the opening of said envelope is provided with fastener means including a groove extending along one edge of the envelope and a projection extending along the opposing edge of the envelope to be firmly received in said groove.

12. The deformable bag of claim 1, wherein the opening of said envelope is closed by folding the open end of said envelope and sewing the thus folded end.

13. The deformable bag of claim 1, wherein the opening of said envelope is closed by joining the edge portions of the open end of said envelope by means of an adhesive.

14. The deformable bag of claim 1, wherein the opening of said envelope is closed by tying up the open end of said envelope by a string or cord.

15. The deformable bag of claim 1, wherein said bag is provided with a cord or strip for fixing the bag at a desired position.

16. The deformable bag of claim 15, wherein said cord or strip is provided with a material having a surface with projecting fibers for releasably engaging projecting fibers on another surface.

17. The deformable bag of claim 1, wherein said small pieces of said gel are charged in said envelope so that 50 to 90 vol % of the space defined by said envelope are occupied by said gel.

* * * * *